(12) United States Patent
Govea et al.

(10) Patent No.: US 10,525,257 B2
(45) Date of Patent: Jan. 7, 2020

(54) ORIENTATION MARKER FOR IMPLANTABLE LEADS AND LEADS, SYSTEMS, AND METHODS UTILIZING THE ORIENTATION MARKER

(71) Applicant: Boston Scientific Neuromodulation Corporation, Valencia, CA (US)

(72) Inventors: Michael X. Govea, Castaic, CA (US); G. Karl Steinke, Valencia, CA (US); Hemant Bokil, Santa Monica, CA (US); Peter J. Yoo, Burbank, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 0 days.

(21) Appl. No.: 15/729,424

(22) Filed: Oct. 10, 2017

(65) Prior Publication Data
US 2018/0104472 A1 Apr. 19, 2018

Related U.S. Application Data

(60) Provisional application No. 62/408,392, filed on Oct. 14, 2016.

(51) Int. Cl.
*A61N 1/05* (2006.01)
*A61N 1/36* (2006.01)
(Continued)

(52) U.S. Cl.
CPC ............... *A61N 1/05* (2013.01); *A61B 90/39* (2016.02); *A61N 1/0551* (2013.01);
(Continued)

(58) Field of Classification Search
CPC ...... A61N 1/05; A61N 1/3605; A61N 1/0551; A61B 2090/3966
See application file for complete search history.

(56) References Cited

U.S. PATENT DOCUMENTS

| 6,181,969 B1 | 1/2001 | Gord |
| 6,516,227 B1 | 2/2003 | Meadows et al. |

(Continued)

OTHER PUBLICATIONS

U.S. Appl. No. 15/783,807, filed Oct. 13, 2017.
International Search Report and Written Opinion for PCT Application No. PCT/US2017/055943 dated Jan. 2. 2018.

*Primary Examiner* — Alyssa M Alter
(74) *Attorney, Agent, or Firm* — Lowe Graham Jones PLLC; Bruce E. Black

(57) ABSTRACT

An implantable electrical stimulation lead includes a lead body; terminals disposed along the proximal portion of the lead body; electrodes disposed along the distal portion of the lead body, the electrodes including at least one segmented electrode; and an asymmetric marker disposed along the distal portion of the lead body and including a first ring and a longitudinal band extending longitudinally from the first ring. The asymmetric marker and lead body are formed of different materials that are distinguishable from each other in the radiological images to facilitate radiological determination of the rotational orientation of the lead when implanted. The marker may also include one or more of a longitudinal extension, a second ring, and non-straight longitudinal edges. The marker may also include the longitudinal band and longitudinal extension without a ring.

19 Claims, 4 Drawing Sheets

(51) Int. Cl.
*A61B 90/00* (2016.01)
*A61N 1/372* (2006.01)

(52) U.S. Cl.
CPC ....... *A61N 1/36003* (2013.01); *A61N 1/3605* (2013.01); *A61N 1/36007* (2013.01); *A61B 2090/3966* (2016.02); *A61N 1/0534* (2013.01); *A61N 1/37235* (2013.01)

(56) References Cited

U.S. PATENT DOCUMENTS

| | | |
|---|---|---|
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 7,244,150 B1 | 7/2007 | Brase et al. |
| 7,437,193 B2 | 10/2008 | Parramon et al. |
| 7,450,997 B1 | 11/2008 | Pianca et al. |
| 7,650,184 B2 | 1/2010 | Walter |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,326,433 B2 | 12/2012 | Blum et al. |
| 8,364,278 B2 | 1/2013 | Pianca et al. |
| 8,391,985 B2 | 3/2013 | McDonald |
| 8,473,061 B2 | 6/2013 | Moffitt et al. |
| 8,571,665 B2 | 10/2013 | Moffitt et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,849,632 B2 | 9/2014 | Sparks et al. |
| 8,958,615 B2 | 2/2015 | Blum et al. |
| 9,037,256 B2 | 5/2015 | Bokil et al. |
| 2007/0150036 A1 | 6/2007 | Anderson |
| 2009/0187222 A1 | 7/2009 | Barker |
| 2009/0204192 A1* | 8/2009 | Carlton ................. A61N 1/0529 607/116 |
| 2009/0276021 A1 | 11/2009 | Meadows et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2010/0030298 A1 | 2/2010 | Martens et al. |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0257707 A1 | 10/2011 | Kothandaraman |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0314919 A1 | 12/2012 | Sparks et al. |
| 2012/0314924 A1 | 12/2012 | Carlton et al. |
| 2012/0316615 A1 | 12/2012 | DiGiore et al. |
| 2013/0039550 A1 | 2/2013 | Blum et al. |
| 2013/0105071 A1 | 5/2013 | DiGiore et al. |
| 2013/0116744 A1 | 5/2013 | Blum et al. |
| 2013/0197424 A1 | 8/2013 | Bedenbaugh |
| 2013/0197602 A1 | 8/2013 | Pianca et al. |
| 2013/0267837 A1 | 10/2013 | Schulte et al. |
| 2014/0039587 A1 | 2/2014 | Romero |
| 2014/0122379 A1 | 5/2014 | Moffitt et al. |
| 2014/0228921 A1 | 8/2014 | Howard |
| 2014/0257428 A1 | 9/2014 | Zhu |
| 2014/0257444 A1* | 9/2014 | Cole ................. A61N 1/08 607/116 |
| 2014/0276002 A1 | 9/2014 | West et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2014/0371819 A1 | 12/2014 | Goetz et al. |
| 2015/0018915 A1 | 1/2015 | Leven |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0151113 A1 | 6/2015 | Govea et al. |
| 2015/0157851 A1 | 6/2015 | Sefkow et al. |
| 2016/0030749 A1 | 2/2016 | Carcieri et al. |
| 2016/0228692 A1 | 8/2016 | Steinke et al. |
| 2017/0056678 A1 | 3/2017 | Bokil |
| 2017/0061627 A1 | 3/2017 | Bokil |

\* cited by examiner

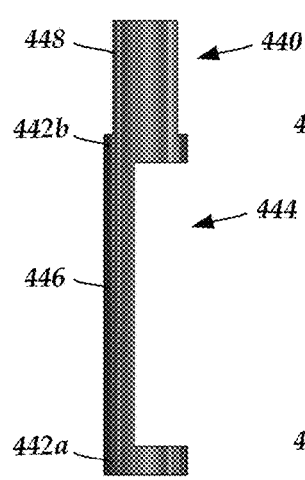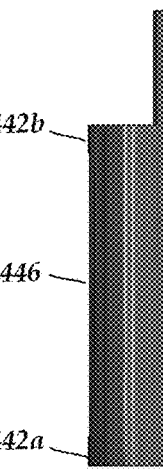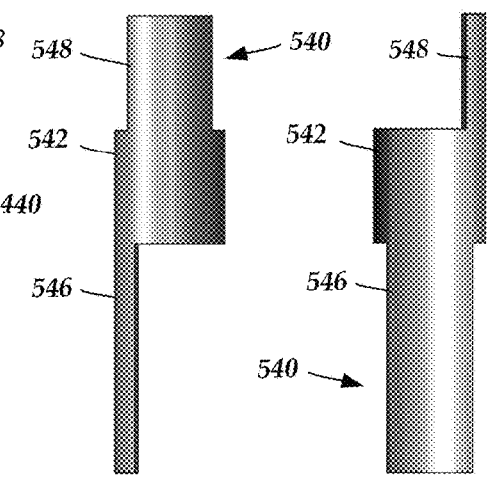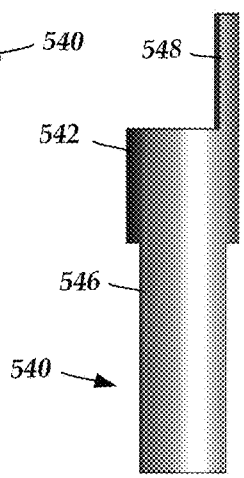
Fig. 4A  Fig. 4B  Fig. 5A  Fig. 5B
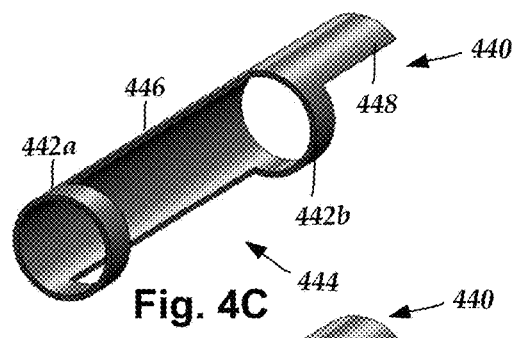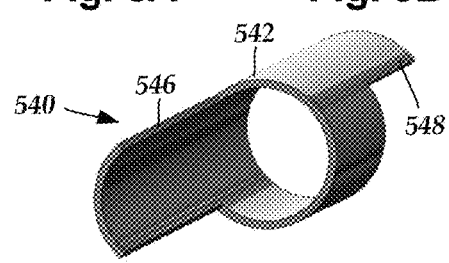
Fig. 4C  Fig. 5C
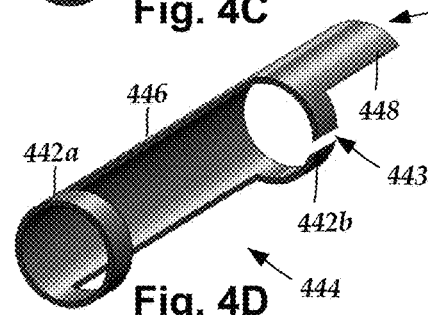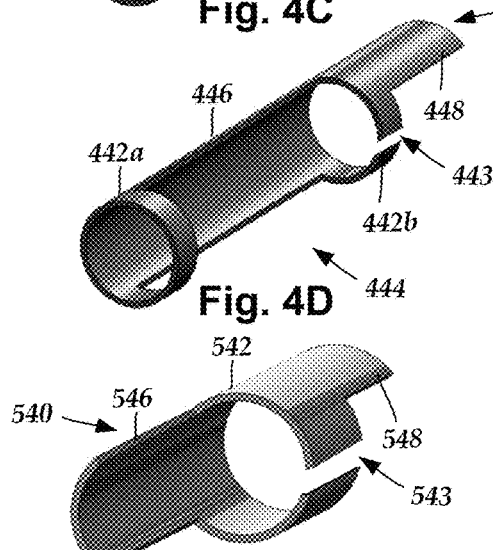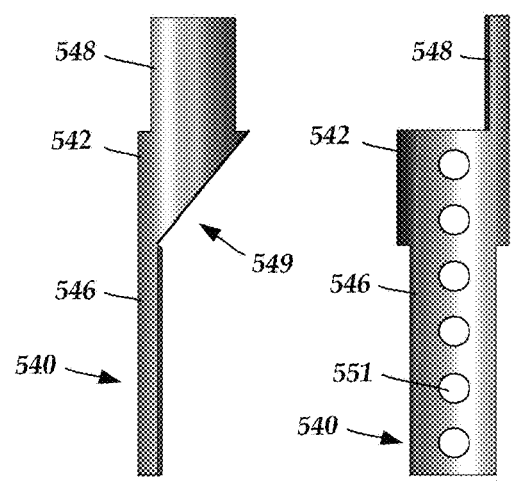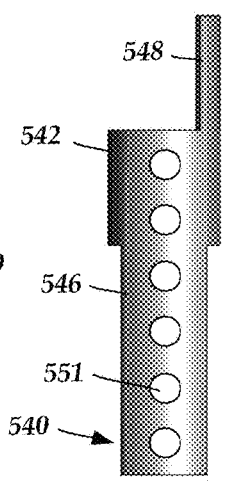
Fig. 4D  Fig. 5D  Fig. 5E  Fig. 5F

ORIENTATION MARKER FOR IMPLANTABLE LEADS AND LEADS, SYSTEMS, AND METHODS UTILIZING THE ORIENTATION MARKER

CROSS-REFERENCE TO RELATED APPLICATIONS

This application claims the benefit under 35 U.S.C. § 119(e) of U.S. Provisional Patent Application Ser. No. 62/408,392, filed Oct. 14, 2016, which is incorporated herein by reference. This application is related to U.S. Provisional Patent Application Ser. No. 62/209,001, filed Aug. 24, 2015; U.S. Provisional Patent Application Ser. No. 62/212,775, filed Sep. 1, 2015; and U.S. Provisional Patent Application Ser. No. 62/408,399, filed on Oct. 14, 2016, all of which are incorporated herein by reference in their entirety.

FIELD

The present invention is directed to the area of implantable electrical stimulation systems and methods of making and using the systems. The present invention is also directed to systems and methods for determining the orientation of an implanted electrical stimulation lead.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an implantable electrical stimulation lead that includes a lead body having a perimeter, a distal portion. and proximal portion; terminals disposed along the proximal portion of the lead body; electrodes disposed along the distal portion of the lead body, the electrodes including at least one segmented electrode, where at least one of the segmented electrodes extends around no more than 50% of the perimeter of the lead body; and an asymmetric marker disposed along the distal portion of the lead body and including a first ring and a longitudinal band extending longitudinally from the first ring and extending around no more than 80% of the perimeter of the lead body. The asymmetric marker and lead body are formed of different materials that are distinguishable from each other in the radiological images. The marker is arranged on the lead body so that a rotational orientation of the lead when implanted can be determined radiologically by observation of the marker.

In at least some embodiments, the first ring has a slit through the ring. In at least some embodiments, the marker further includes a second ring, wherein the longitudinal band extends between the first and second rings. In at least some embodiments, the first or second ring (or both rings) include a slit through that ring.

In at least some embodiments, the marker further includes a longitudinal extension extending longitudinally from the first ring away from the longitudinal band, wherein the longitudinal extension extends around no more than 80% of the perimeter of the lead body. In at least some embodiments, the longitudinal band extends distally from the first ring and the longitudinal extension extends proximally from the first ring.

Another embodiment is an implantable electrical stimulation lead including a lead body having a perimeter, a distal portion. and proximal portion; a plurality of terminals disposed along the proximal portion of the lead body; electrodes disposed along the distal portion of the lead body, the electrodes including at least one segmented electrode, wherein at least one of the segmented electrodes extends around no more than 50% of the perimeter of the lead body; and an asymmetric marker disposed along the distal portion of the lead body and including a longitudinal band and a longitudinal extension extending longitudinally away from the longitudinal band, wherein each of the longitudinal band and the longitudinal extension individually extend around no more than 80% of the perimeter of the lead body, wherein the longitudinal band and the longitudinal extension are circumferentially offset from each other, wherein the asymmetric marker and lead body are formed of different materials that are distinguishable from each other in the radiological images, wherein the marker is arranged on the lead body so that a rotational orientation of the lead when implanted can be determined radiologically by observation of the marker.

In at least some embodiments, both the longitudinal band and the longitudinal extension extend around no more than 30% of the perimeter of the lead body. In at least some embodiments, the longitudinal band and the longitudinal extension are circumferentially offset from each other. In at least some embodiments, the longitudinal band and the longitudinal extension differ in circumferential width by at least 10% of the circumferential width of the longitudinal band. In at least some embodiments, the longitudinal band and the longitudinal extension differ in longitudinal length by at least 10% of the longitudinal length of the longitudinal band.

In at least some embodiments, the longitudinal band extends around no more than 30% of the perimeter of the lead body. In at least some embodiments, a circumferential width of the longitudinal band varies along a longitudinal length of the longitudinal band. In at least some embodiments, the longitudinal band has a first end coupled to the first ring and a second end spaced apart longitudinally from the first end, wherein the circumferential width is narrowest at a position between the first end and the second end. In at least some embodiments, the longitudinal band has a first end coupled to the first ring and a second end spaced apart longitudinally from the first end, wherein the circumferential width is widest at a position between the first end and the second end.

In at least some embodiments, the longitudinal band has two longitudinal edges extending longitudinally away from the first ring, wherein at least one of those longitudinal edges is not straight. In at least some embodiments, both of the longitudinal edges are not straight. In at least some embodiments, the longitudinal band defines a notch in the longitudinal band. In at least some embodiments, the longitudinal band is aligned with at least one of the segmented electrodes.

Another embodiment is an electrical stimulation system that includes any of the leads described above and a control module coupleable to the lead, the control module including a housing, and an electronic subassembly disposed in the housing. In at least some embodiments, the system further includes a lead extension coupleable between the lead and the control module.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic side view of a second embodiment of an asymmetric marker, according to the invention;

FIG. 4B is a schematic rotated view of the asymmetric marker of FIG. 4A, according to the invention;

FIG. 4C is a schematic perspective view of the asymmetric marker of FIG. 4A, according to the invention;

FIG. 4D is a schematic perspective view of a third embodiment of an asymmetric marker, according to the invention;

FIG. 5A is a schematic side view of a fourth embodiment of an asymmetric marker, according to the invention;

FIG. 5B is a schematic rotated view of the asymmetric marker of FIG. 5A, according to the invention;

FIG. 5C is a schematic perspective view of the asymmetric marker of FIG. 5A, according to the invention;

FIG. 5D is a schematic perspective view of a fifth embodiment of an asymmetric marker, according to the invention;

FIG. 5E is a schematic side view of a sixth embodiment of an asymmetric marker, according to the invention;

FIG. 5F is a schematic side view of a seventh embodiment of an asymmetric marker, according to the invention;

FIG. 6A is a schematic side view of an eighth embodiment of an asymmetric marker, according to the invention;

FIG. 6B is a schematic rotated view of the asymmetric marker of FIG. 6A, according to the invention;

FIG. 6C is a schematic perspective view of the asymmetric marker of FIG. 6A, according to the invention.

DETAILED DESCRIPTION

The present invention is directed to the area of implantable electrical stimulation systems and methods of making and using the systems. The present invention is also directed to systems and methods for determining the orientation of an implanted electrical stimulation lead.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181, 969; 6,516,227; 6,609,029; 6,609,032; 6,741,892; 7,244, 150; 7,450,997; 7,672,734; 7,761,165; 7,783,359; 7,792, 590; 7,809,446; 7,949,395; 7,974,706; 8,175,710; 8,224, 450; 8,271,094; 8,295,944; 8,364,278; 8,391,985; and 8,688,235; and U.S. Patent Applications Publication Nos. 2007/0150036; 2009/0187222; 2009/0276021; 2010/ 0076535; 2010/0268298; 2011/0005069; 2011/0004267; 2011/0078900; 2011/0130817; 2011/0130818; 2011/ 0238129; 2011/0313500; 2012/0016378; 2012/0046710; 2012/0071949; 2012/0165911; 2012/0197375; 2012/ 0203316; 2012/0203320; 2012/0203321; 2012/0316615; 2013/0105071; and 2013/0197602, all of which are incorporated by reference in their entirety. In the discussion below, a percutaneous lead will be exemplified, but it will be understood that the methods and systems described herein are also applicable to paddle leads and other leads.

A percutaneous lead for electrical stimulation (for example, deep brain or spinal cord stimulation) includes stimulation electrodes that can be ring electrodes, segmented electrodes that extend only partially around the perimeter of the lead, or any other type of electrode, or any combination thereof. The segmented electrodes can be provided in sets of electrodes, with each set having electrodes circumferentially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves, muscles, and tissues.

Figure 1:
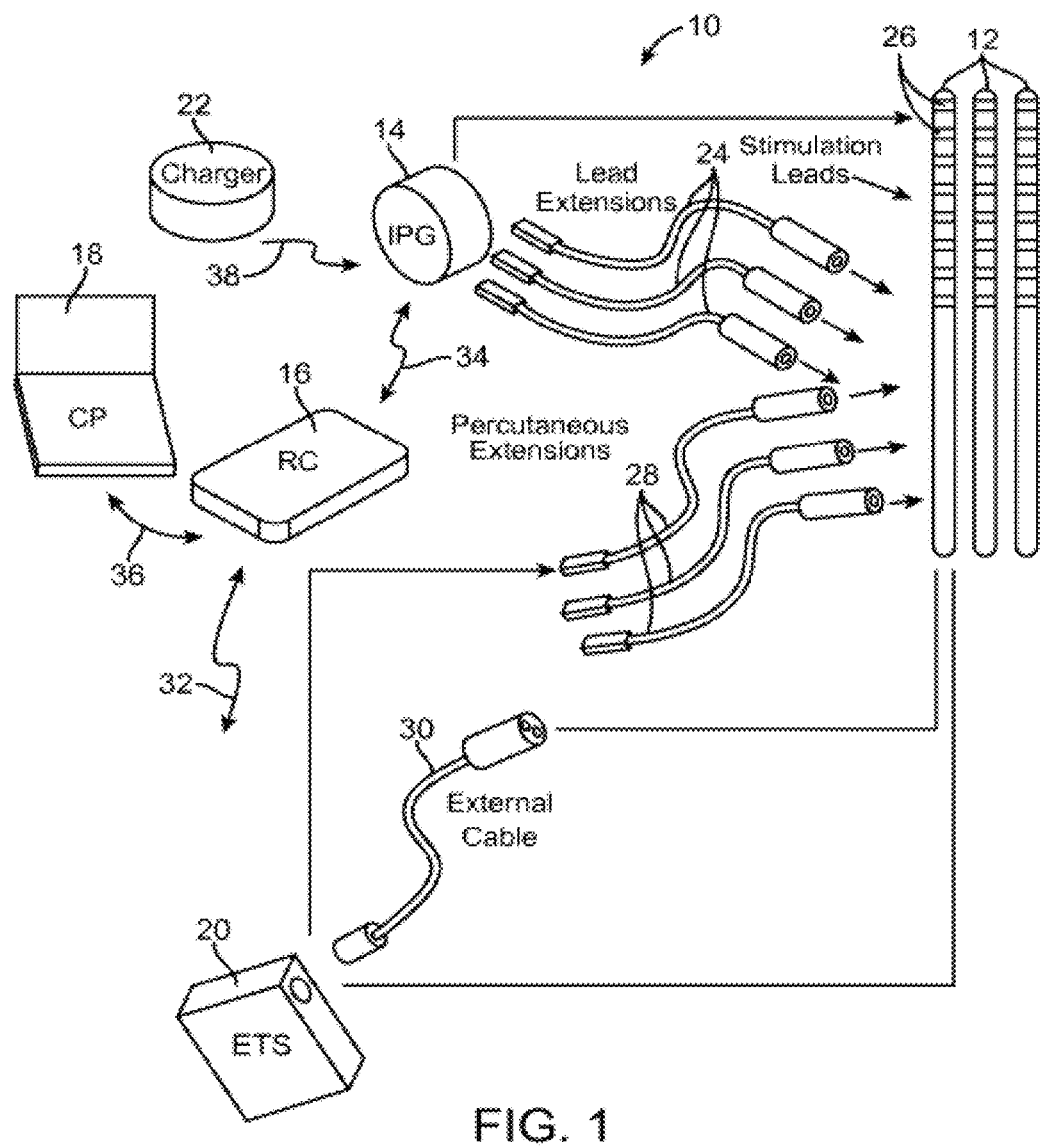
FIG. 1 is a schematic view of one embodiment of an electrical stimulation system, according to the invention.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference in its entirety. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference in their entirety.

Figure 2:
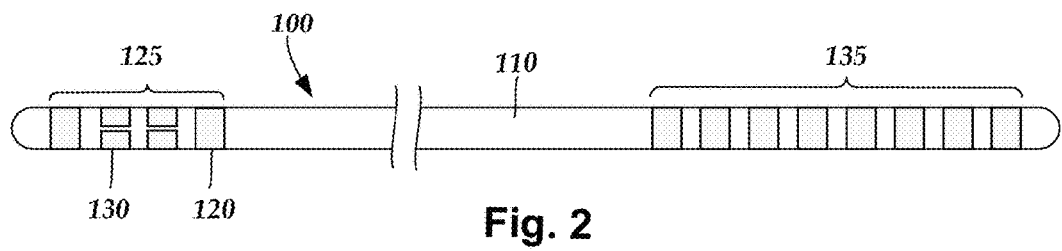
FIG. 2 is a schematic side view of one embodiment of an electrical stimulation lead, according to the invention.

FIG. 2 illustrates one embodiment of a lead 110 with electrodes 125 disposed at least partially about a perimeter of the lead 110 along a distal end portion of the lead and terminals 135 disposed along a proximal end portion of the lead.

The lead 110 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of a stylet (not shown). The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, advance the lead 110, retract the lead 110, or rotate the lead 110.

In some embodiments, measurement devices coupled to the muscles or other tissues stimulated by the target neurons, or a unit responsive to the patient or clinician, can be coupled to the implantable pulse generator or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the perimeter of the lead 110 to stimulate the target neurons. Stimulation electrodes may be ring-shaped so that current projects from each electrode equally in every direction from the position of the electrode along a length of the lead 110. In the embodiment of FIG. 2, two of the electrodes 125 are ring electrodes 120. Any number of ring electrodes 120 can be disposed along the length of the lead body 110 including, for example, one, two three, four, five, six, seven, eight, nine, ten, eleven, twelve, thirteen, fourteen, fifteen, sixteen or more ring electrodes 120. The distal-most ring electrode 120 may be a tip electrode (see, e.g., electrode 320a of FIG. 3) which covers most, or all, of the distal tip of the lead.

Ring electrodes typically do not enable stimulus current to be directed from only a limited angular range around of the lead. Segmented electrodes 130, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead). To achieve current steering, segmented electrodes can be utilized in addition to, or as an alternative to, ring electrodes.

The lead 100 includes a lead body 110, terminals 135, and one or more ring electrodes 120 and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a perimeter of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent application Ser. Nos. 14/557,211 and 14/286,797; and U.S. Provisional Patent Application Ser. No. 62/113,291, all of which are incorporated herein by reference in their entirety.

The lead 100 in FIG. 2 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes 130 may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110. When the lead 100 includes both ring electrodes 120 and segmented electrodes 130, the ring electrodes 120 and the segmented electrodes 130 may be arranged in any suitable configuration.

Conductor wires that attach to the ring electrodes 120 or segmented electrodes 130 extend along the lead body 110. These conductor wires may extend through the material of the lead 100 or along one or more lumens defined by the lead 100, or both. The conductor wires couple the electrodes 120, 130 to the terminals 135.

In many instances, it is important to identify the rotational orientation of a lead with segmented electrodes when the lead is implanted into the patient (for example, in the brain of a patient.) Knowing the rotational orientation of the lead (and, in particular, the rotational orientation of the individual segmented electrodes) will facilitate determining which segmented electrodes may be situated for stimulating a particular anatomical or physiological tissue target or determining an expected direction of the electrical stimulation field that can be generated by each of the segmented electrodes. It may be difficult to determine orientation radiologically because the segmented electrodes at least longitudinal position will often overlap in a radiological image.

Figure 3:
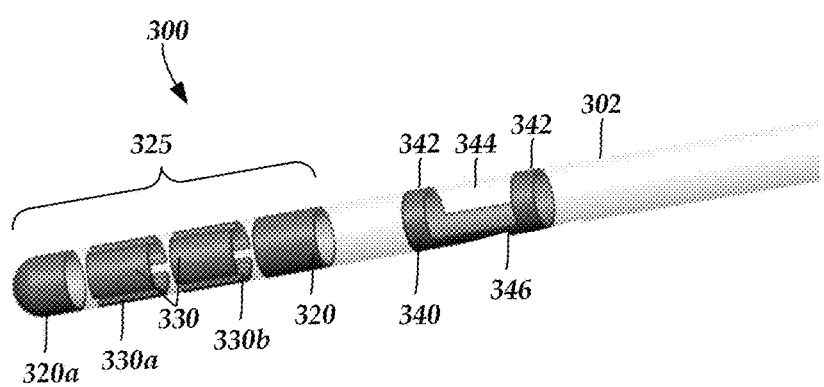
FIG. 3 is a schematic side view of one embodiment of the distal portion of a lead with an asymmetric marker, according to the invention.

To facilitate radiological identification of rotational orientation, the lead can include a rotationally asymmetric marker made of different material (for example, a conductive material such as metal) from the lead body so that the marker and lead body are radiologically distinguishable. FIG. 3 illustrates one example of a distal portion of a lead 300 with a lead body 302 and electrodes 325 including one or more optional ring electrodes 320, 320a and multiple segmented electrodes 330. The lead 300 also includes a marker 340 that is asymmetrically shaped. The marker 340 is made of a material that is substantially different from the material of the lead body 302, particularly, when viewed using a radiological imaging technique, such as CT imaging, so that the marker is radiologically distinguishable from the lead body. In at least some embodiments, the marker 340 is made of metal (such as a pure metal or an alloy) and, in at least some embodiments, is made of the same material as the electrodes 325.

The marker 340 defines one or more optional rings 342 formed around the entire perimeter of the lead 300, at least one window 344, and a longitudinal band 346 disposed opposite the window. In at least some embodiments, the longitudinal band 346 of the marker 340 extends around no more than 80%, 75%, 67%, 60%, 50%, 40%, 34%, 30%, 25%, or 20% of the perimeter of the lead with the window 344 extending around the remainder of the perimeter. In at least some embodiments, to further facilitate the determination of directionality of the marker 340, the longitudinal band 346 will extend around less than half the perimeter of the lead and may extend around no more than one third or one quarter of the perimeter. In at least some embodiments, the longitudinal band 346 of the marker 340 is aligned with at least one of the segmented electrodes 330 (such as segmented electrodes 330a, 330b in the illustrated embodiment of FIG. 3.) In the illustrated embodiments, the longitudinal band 346 extends between two rings 342.

FIGS. 4A-4C illustrate another embodiment of a marker 440 with two rings 442a, 442b, a window 444, a longitudinal band 446 opposite the window, and a longitudinal extension 448 extending from one of the rings 442b. The arrangement and design considerations described above for rings 342, window 344, and longitudinal band 346 are also applicable to rings 442a, 442b, window 444, and longitudinal band 446.

In the illustrated embodiment, the longitudinal extension 448 extends from the proximal ring 442b, but in other embodiments the longitudinal extension can extend from the distal ring 442a. In yet other embodiments, the marker can have two longitudinal extensions which each extend from a different one of the rings. In at least some embodiments, the longitudinal extension 448 of the marker 440 extends around no more than 80%, 75%, 67%, 60%, 50%, 40%, 34%, 30%, 25%, or 20% of the perimeter of the lead. In at least some embodiments, to further facilitate the determination of directionality of the marker 440, the longitudinal extension 448 will extend around less than half the perimeter of the lead and may extend around no more than one third or one quarter of the perimeter. In at least some embodiments, the longitudinal extension 448 of the marker 440 is aligned with at least one of the segmented electrodes (such as one of segmented electrodes 330a, 330b in the illustrated embodiment of FIG. 3.)

In at least some embodiments, the circumferential width of the longitudinal extension 448 is the same as the circumferential width of the longitudinal band 446. In other embodiments, the circumferential width of the longitudinal extension 448 is larger (for example, by at least 10%, 20%, 25% or more of the longitudinal band) or smaller (for example, by at least 10%, 20%, 25% or more of the longitudinal band) than the circumferential width of the longitudinal band 446. In addition, the longitudinal extension 448 and longitudinal band 446 can have a same or different shape.

In at least some embodiments, a longitudinal length of the longitudinal band 446 is different from the longitudinal length of the longitudinal extension 448. In the illustrated embodiment, the longitudinal band 446 is longer (optionally, by at least 10, 20, 30, 40, or 50% or more of the longitudinal band) than the longitudinal extension 448. It will be recognized that in other embodiments, the longitudinal extension is longer (optionally, by at least 10, 20, 30, 40, or 50% or more of the longitudinal band) than the longitudinal band.

In at least some embodiments, to facilitate directional determination of the lead, the longitudinal extension 448 will be circumferentially offset from the longitudinal band 446 by at least 30, 45, 60, 90, 100, 120, 140, 160, or 180 degrees. In at least some embodiments, as illustrated in FIGS. 4A-4C, the longitudinal extension 448 and longitudinal band 446 are circumferentially offset so that they are positioned around non-overlapping portions of the perimeter of the lead (which may or may not share a starting/ending point). It has been found that the marker 340 of FIG. 3 requires either a CT scan or two perpendicular planar images (for example, planar x-ray or fluoroscopic images) to determine the orientation of the lead. By circumferentially offsetting the longitudinal extension 448 from the longitudinal band 446 in the marker 440, a single planar image (for example, a single x-ray or fluoroscopic image), in a plane that includes or is parallel to the longitudinal axis of the lead, may be all that is needed for determining lead orientation.

FIG. 4D illustrates another embodiment of the marker 440 where the proximal ring 442b is a partial ring with a slit 443 through the ring. Unless otherwise indicated, any ring of the markers described herein can be full rings or partial rings with one or more slits through the ring. The slit 443 can extend through the entire longitudinal width of the ring, as illustrated in FIG. 4D, or only partway along the longitudinal width of the ring. Also, it will be recognized that other markers can be formed with only a single ring (see, for example, FIGS. 5A-5F) or no rings.

FIGS. 5A-5C illustrate a further embodiment of a marker 540 with a single ring 542, a longitudinal band 546 extending distally from the ring 542, and a longitudinal extension 548 extending proximally from the ring 542. Unless otherwise indicated, the arrangement and design considerations described above for rings 342, 442a, 442b; longitudinal bands 346, 446; and longitudinal extension 448 are also applicable to ring 542, longitudinal band 546, and longitudinal extension 548. In the illustrated embodiments, the longitudinal extension 548 and longitudinal band 546 are circumferentially offset so that they are positioned around non-overlapping portions of the perimeter of the lead (which may or may not share a starting/ending point). Also, in the illustrated embodiment, the longitudinal band 546 is longer than the longitudinal extension 548, although in other embodiments they may have equal lengths or the longitudinal band may be shorter than the longitudinal extension. As indicated above, the arrangement, position, and lengths of the longitudinal band and longitudinal extension can be modified to provide other suitable embodiments.

FIG. 5D illustrates another embodiment of the marker 540 where the ring 542 is a partial ring with a slit 543 through the ring. FIG. 5E illustrates yet another embodiment where the ring 542 has a slit 549 that only extends partway through the ring (and, in the illustrated embodiment, forms a notch in the ring). FIG. 5F illustrates a further embodiment with one or more apertures 551 in the ring 542, the longitudinal band 548, or both. Alternatively or additionally, apertures 551 can be positioned in the longitudinal extension 548. The apertures 551 may facilitate maintaining attachment of the marker to the lead body, particularly, if a portion of the lead body extends into or through the aperture. The one or more apertures can have any suitable shape including, but not limited to, round, square, rectangular, triangular, hexagonal, octagonal, or any other regular or irregular shape.

FIGS. 6A-6C illustrate yet another embodiment of a marker 640 with two rings 642a, 642b, a window 644, and a longitudinal band 646 opposite the window. The arrangement and design considerations described above for rings 342, window 344, and longitudinal band 346 are also applicable to rings 642a, 642b, window 644, and longitudinal band 646. In this embodiment, the circumferential width of the longitudinal band 646 varies along the longitudinal length of the longitudinal band. In the illustrated embodiment, this variation forms a notch 647 in the longitudinal band 646. In at least some embodiments, including the illustrated embodiment of FIGS. 6A-6C, one or both of the longitudinal edges 645a, 645b of the longitudinal band are not straight. Similar to the markers 440, 540, the marker 640 may facilitate the use of a single planar image single planar image (for example, a single x-ray or fluoroscopic image), in a plane that includes or is parallel to the longitudinal axis of the lead, for determining lead orientation.

Figure 6D:
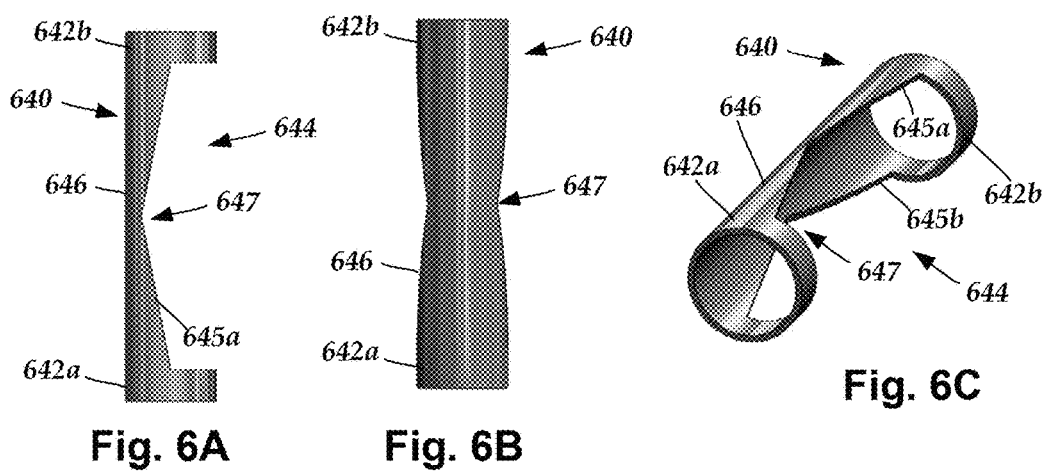
FIG. 6D is a schematic perspective view of a ninth embodiment of an asymmetric marker, according to the invention.
Figure 6D:
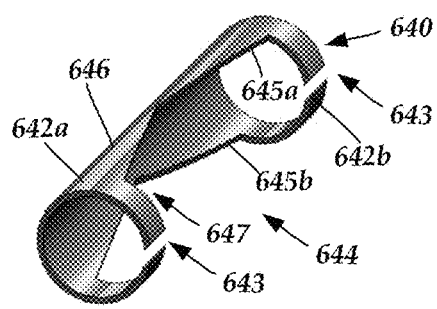

FIG. 6D illustrates another embodiment of the marker 640 where the rings 642a, 642b are both partial rings with a slit 643 through each ring. It will be recognized that in other embodiments, only one of the rings 642a, 642b includes a slit.

In the illustrated embodiment, the longitudinal band 646 narrows from both ends to a narrowest portion in the center of the longitudinal band. In other embodiments, the narrowest portion may be at any other portion of the longitudinal band. In yet other embodiments, instead of narrowing, the longitudinal band may widen towards to center or any other position along the longitudinal band. In yet other embodiments, the longitudinal band may have any arrangement of narrower and wider portions or any other arrangement of one or more non-straight longitudinal edges.

It will be understood that the longitudinal band 646 may also be modified to include a longitudinal extension (such as longitudinal extensions 448, 548) or modified to remove one of the rings 642a, 642b, or any combination of the modifications described in this paragraph. Moreover, any of the embodiments illustrated in FIGS. 4A-5C can be modified to include one or more non-straight longitudinal edges along the longitudinal band or longitudinal extension (or both).

The markers described herein are made of a radiopaque material such as metals or radiopaque plastics or composites. The markers can be made by any suitable method including, but not limited to, machining, molding, casting or the like. The markers can be coupled to a lead in any suitable manner including in the same or similar manner to the coupling of electrodes or terminals to a lead.

Radiological imaging, such as computed tomography (CT), x-ray, or fluoroscopic imaging, can be used to identify the orientation of the lead due to the asymmetry of the marker. The use of an asymmetrical marker (such as marker 340, 440, 540, 640) on the lead aids in the identification of the rotational orientation of the lead using imaging techniques, such as CT imaging or other radiological imaging techniques. Examples of methods and systems for identifying lead orientation using radiological imaging and the markers described above are presented in U.S. Provisional Patent Application Ser. Nos. 62/209,001 and 62/212,775 and U.S. Provisional Patent Application Ser. No. 62/408,399, all of which are incorporated herein by reference in their entirety. In other embodiments, a single planar image of a lead with marker 440, 540, 640 can be used to determine lead orientation.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. An implantable electrical stimulation lead, comprising:
   a lead body having a perimeter, a distal portion, and proximal portion;
   a plurality of terminals disposed along the proximal portion of the lead body;
   a plurality of electrodes disposed along the distal portion of the lead body, the plurality of electrodes comprising at least one segmented electrode, wherein at least one of the at least one segmented electrode extends around no more than 50% of the perimeter of the lead body; and
   an asymmetric marker disposed along the distal portion of the lead body and comprising a first ring, a longitudinal band extending longitudinally from the first ring and extending around no more than 80% of the perimeter of the lead body, and a longitudinal extension extending longitudinally from the first ring away from the longitudinal band, wherein the longitudinal extension extends around no more than 80% of the perimeter of the lead body, wherein the longitudinal band and the longitudinal extension are circumferentially offset from each other, wherein the asymmetric marker and lead body are formed of different materials that are distinguishable from each other in radiological images, wherein the asymmetric marker is arranged on the lead body so that a rotational orientation of the lead when implanted can be determined radiologically by observation of the asymmetric marker.

2. The lead of claim 1, wherein the asymmetric marker further comprises a second ring, wherein the longitudinal band extends between the first and second rings.

3. The lead of claim 1, wherein both the longitudinal band and the longitudinal extension extend around no more than 30% of the perimeter of the lead body.

4. The lead of claim 3, wherein the longitudinal band and the longitudinal extension differ in circumferential width by at least 10% of the circumferential width of the longitudinal band.

5. The lead of claim 1, wherein the longitudinal band and the longitudinal extension differ in longitudinal length by at least 10% of the longitudinal length of the longitudinal band.

6. The lead of claim 1, wherein the longitudinal band extends distally from the first ring and the longitudinal extension extends proximally from the first ring.

7. The lead of claim 1, wherein the longitudinal band extends around no more than 30% of the perimeter of the lead body.

8. The lead of claim 1, wherein a circumferential width of the longitudinal band varies along a longitudinal length of the longitudinal band.

9. The lead of claim 8, wherein the longitudinal band has a first end coupled to the first ring and a second end spaced apart longitudinally from the first end, wherein the circumferential width is narrowest at a position between the first end and the second end.

10. The lead of claim 8, wherein the longitudinal band has a first end coupled to the first ring and a second end spaced apart longitudinally from the first end, wherein the circumferential width is widest at a position between the first end and the second end.

11. The lead of claim 8, wherein the longitudinal band has two longitudinal edges extending longitudinally away from the first ring, wherein at least one of those longitudinal edges is not straight.

12. The lead of claim 11, wherein both of the longitudinal edges are not straight.

13. The lead of claim 8, wherein the longitudinal band defines a notch in the longitudinal band.

14. The lead of claim 8, wherein the asymmetric marker further comprises a second ring, wherein the longitudinal band extends between the first and second rings.

15. The lead of claim 1, wherein the longitudinal band is aligned with at least one of the at least one segmented electrode.

16. An implantable electrical stimulation lead, comprising:
- a lead body having a perimeter, a distal portion, and proximal portion;
- a plurality of terminals disposed along the proximal portion of the lead body;
- a plurality of electrodes disposed along the distal portion of the lead body, the plurality of electrodes comprising at least one segmented electrode, wherein at least one of the at least one segmented electrode extends around no more than 50% of the perimeter of the lead body; and
- an asymmetric marker disposed along the distal portion of the lead body and comprising a longitudinal band and a longitudinal extension extending longitudinally away from the longitudinal band, wherein each of the longitudinal band and the longitudinal extension individually extend around no more than 80% of the perimeter of the lead body, wherein the longitudinal band and the longitudinal extension are circumferentially offset from each other, wherein the asymmetric marker and lead body are formed of different materials that are distinguishable from each other in radiological images, wherein the asymmetric marker is arranged on the lead body so that a rotational orientation of the lead when implanted can be determined radiologically by observation of the asymmetric marker.

17. An electrical stimulation system, comprising:
the lead claim 1; and
a control module coupleable to the lead, the control module comprising
a housing, and
an electronic subassembly disposed in the housing.

18. The lead of claim 16, wherein both the longitudinal band and the longitudinal extension extend around no more than 30% of the perimeter of the lead body.

19. The lead of claim 16, wherein the longitudinal band and the longitudinal extension differ in circumferential width by at least 10% of the circumferential width of the longitudinal band.

* * * * *